US009925134B2

(12) United States Patent
Rival et al.

(10) Patent No.: US 9,925,134 B2
(45) Date of Patent: Mar. 27, 2018

(54) USE OF SUBSTANCES TO PROTECT FGF-2 OR FGF-BETA GROWTH FACTOR

(75) Inventors: Delphine Rival, Ternay (FR); Sebastien Bonnet, Lyons (FR); Isabelle Orly, Irigny (FR); Eric Perrier, Les Cotes d'Arey (FR)

(73) Assignee: BASF Beauty Care Solutions France SAS, Lyons (FR)

( * ) Notice: Subject to any disclaimer, the term of this patent is extended or adjusted under 35 U.S.C. 154(b) by 62 days.

(21) Appl. No.: 11/803,805

(22) Filed: May 16, 2007

(65) Prior Publication Data

US 2008/0089906 A1  Apr. 17, 2008

(51) Int. Cl.
| | |
|---|---|
| A61K 36/185 | (2006.01) |
| A61K 8/97 | (2017.01) |
| A61K 36/31 | (2006.01) |
| A61K 36/8998 | (2006.01) |
| A61Q 19/00 | (2006.01) |
| G01N 33/557 | (2006.01) |
| A61Q 1/06 | (2006.01) |
| A61Q 5/02 | (2006.01) |
| A61Q 19/04 | (2006.01) |
| A61Q 19/08 | (2006.01) |
| A61Q 19/10 | (2006.01) |

(52) U.S. Cl.
CPC .............. *A61K 8/97* (2013.01); *A61K 36/185* (2013.01); *A61K 36/31* (2013.01); *A61K 36/8998* (2013.01); *A61Q 19/00* (2013.01); *G01N 33/557* (2013.01); *A61K 2800/91* (2013.01); *A61Q 1/06* (2013.01); *A61Q 5/02* (2013.01); *A61Q 19/04* (2013.01); *A61Q 19/08* (2013.01); *A61Q 19/10* (2013.01); *G01N 2333/503* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 5,705,170 A | 1/1998 | Kong et al. | |
| 2005/0063932 A1 | 3/2005 | Dilallo et al. | |
| 2005/0255059 A1* | 11/2005 | Oblong et al. | 424/59 |
| 2006/0198800 A1 | 9/2006 | Dilallo et al. | |
| 2007/0110731 A1 | 5/2007 | Riley | 424/93.7 |
| 2007/0122492 A1* | 5/2007 | Behr et al. | 424/725 |
| 2007/0203240 A1* | 8/2007 | Oblong et al. | 514/561 |

FOREIGN PATENT DOCUMENTS

| | | | | |
|---|---|---|---|---|
| JP | 10029922 A | | 2/1998 | |
| JP | 10-029922 | * | 3/1998 | |
| JP | 2005029776 A | | 2/2005 | |
| WO | WO 92/13526 A | | 8/1992 | A61K 9/16 |
| WO | WO 2003/086329 A3 | | 10/2003 | A61K 7/42 |
| WO | WO 2006/080768 A1 | | 8/2006 | A61Q 19/00 |
| WO | WO 2007/034042 | | 3/2007 | A61K 31/192 |

OTHER PUBLICATIONS

Search Report from France for Application No. FR0654316, dated Jul. 31, 2007.
Medline Database Abstract No. XP002444887 abstracting Pei Xian-Wu, et al., "Arnebia root oil promotes wound healing and expressions of basic fibroblast growth factor on the wound surface in rabbits" *Journal of Chinese Integrative Medicine*, 2006, pp. 52-55.
Mani, et al., "Enhancement of wound healing by shikonin analogue 93/637 in normal and impaired healing." *Skin Pharmacology and Physiology*, 2004, vol. 17, No. 1, pp. 49-56.
Fabre de la Ripelle, "Les hibiscus, tradition et modernite" *Phytotherapie*, 2006, vol. 4, No. 3, pp. 136-144.
Search Report from Great Britain for Application No. GB0710263.5, dated Sep. 27, 2007.
EPODOC Abstract abstracting JP 10029922A.
EPODOC Abstract abstracting JP 2003034631A.
EPODOC Abstract abstracting JP 2005104886A.
EPODOC Abstract abstracting JP 10036279A.
Search Report from France for Application No. FR0754725, dated Dec. 13, 2007.
Vemuri, et al., "The Stability of bFGF Against Thermal Denaturation" *Journal of Pharmacy and Pharmacology*, 1994, vol. 46, pp. 481-486.
Matasusaki, et al., "Novel Functional Biodegradable Polymer II: Fibroblast Growth Factor-2 Activities of Poly(γ-glutamic acid)-sulfonate" *Biomacromolecules*, 2005, vol. 6, pp. 400-407.
Zissu et al., "Mise au Point d'un Test pour Évaluer L'Éfficacitté des Crèmes Barrières" *Annales de Dermatologie et de Vénéréologie*, 1994, vol. 121, N. 10, pp. 700-703.
INPI Search Report dated Jan. 19, 2010.
Database WPI Week 199815 Thompson Scientific, London, GB; An 1998-163654, XP002563911 & JP10029922A (Shiseido Co. Ltd) Feb. 3, 1998.
D. Shoo et al, "Two-Stage Solvent Extraction of Seeds of Hibiscus Abelmoschus Linn: Lipid and FA Compositions", Journal of the American Oil Chemists' Society, Springer, Berlin, DE, vol. 80, No. 3, Mar. 1, 2003, pp. 209-211, XP001536610 ISSN: 0003-021X, p. 209, col. 2.
JP10029922A Machine Translation, filed Feb. 3, 1998, Shiseido Co. Ltd., whole document.

* cited by examiner

*Primary Examiner* — Chris R Tate
(74) *Attorney, Agent, or Firm* — Drinker Biddle & Reath LLP (57) ABSTRACT

The invention relates to substances which are capable of protecting FGF-2, to a composition for preventing or controlling degradation of FGF-2, and a method of protecting FGF-2 in the skin from degradation.
In particular, the invention relates to an extract of *Hibiscus Abelmoschus* or ambrette, a rebokza extract, a gougizi berry extract, a banha extract, a *lessonia* extract, a mustard flour extract, a wooyin extract, a barley extract, and/or a sesame extract, in amounts effective to protect FGF-2 from its degradation.
Further, the present invention allows the extracellular matrix to be restructured, particularly at the dermis, which is useful, for example, for controlling aging.

16 Claims, 4 Drawing Sheets

USE OF SUBSTANCES TO PROTECT FGF-2 OR FGF-BETA GROWTH FACTOR

The present invention relates to the development of active ingredients for a cosmetic, dermo-cosmetic or pharmaceutical application, in order to control degradation of at least one growth factor. More particularly, the invention relates to the protection of the degradation of the Fibroblast Growth Factor (FGF-2 or basic FGF or FGF-β).

The present invention further relates to the use of active ingredients preventing, limiting or improving the quality of the derma, notably when the latter is subject to effects of age, notably in a human being.

STATE OF THE ART

Many growth factors are involved at skin level. An example of such a growth factor is FGF-2 which has a wide activity spectrum, including proliferation of fibroblasts which thereby allows synthesis of macromolecules of the matrix which is essential to the integrity of the skin. FGF-2 is protected in the skin by heparan sulfate proteoglycans. In the 1990s, Feige & Baird (*Médecine/Sciences*, 1992; 8:805-10) described the close relationship between growth factors and proteoglycans of the intracellular matrix, explaining that, in addition to a reservoir phenomenon, this interaction protected the growth factors against proteolysis. A higher stability of the growth factors results from this (e.g., a lengthened half-life in vivo), thereby allowing them to optimally fulfill their functions.

FGF-2 and Proteoglycans

FGF-2 is part of a family consisting of 23 different FGFs as counted at the present time. FGF-2 exists in several isoforms. In vertebrates, five isoforms are found with molecular weights of 18; 22; 22.5; 24 and 34 kDa. Only the 18 kDa form is detected outside the cells while the other isoforms are confined inside the cell and more specifically in the nucleus. FGF-2 is an ubiquitous protein which plays a very important role on a physiological level; FGF-2 is involved in embryo development, angiogenesis, neuron differentiation and tissue repair. Indeed, it is present in most tissues with a distribution more particularly targeted at the basal membrane of the latter. Although FGF-2 is present in the organism in a proportion such that it may be purified and characterized, its mRNA is not detectable. This fact and the particularity that it is distributed intimately bound to the basal membrane of the tissues, suggest that it is produced at an initial rate and then released by the cells during the development so as to be stored in the MEC (the basal membrane during this process is subject to intense remodelling allowing FGF-2 to be released locally). This storage would allow FGF-2 to be released in the adult condition, if need be, in order to participate in tissue repair and to maintain differentiated functions. With age, the supply of FGF-2 would therefore decrease while no longer providing maximum activity conditions.

Proteoglycans (PG) form potential reservoirs of the extracellular form of 18 kDa FGF-2 in the extracellular matrix. Proteoglycans are molecules with extracellular, membrane, or intracellular localization. They consist of a protein chain called a "core protein" on which variable glycoaminoglycans (GAG) are grafted. The main GAGs are heparin sulfate (HS); heparin (HP); chondroitin sulfate (CS); dermatan sulfate (DS), an isomer of chondroitin sulfate, and keratin sulfate (KS).

Heparan sulfate proteoglycans (HSPG) were described in the literature for being associated with a relatively strong affinity to FGF-2, protecting it from various degradations and being used as a reservoir. The specific link from FGF-2 to a particular GAG was demonstrated: heparan sulfate. An inhibition of the link of FGF-2 to the MEC of endothelial cells grown in the presence of heparin or heparan sulfate was demonstrated but not in the presence of chrondroitin sulfate, keratan sulfate or hyaluronic acid. Further, absence of a link from FGF-2 to a MEC pretreated with heparitinase (specific enzyme of heparin and heparan sulfate) was revealed but not with chondroitinase ABC (specific enzyme of chondroitin sulfate, keratan sulfate and hyaluronic acid). All these results prove the existence of a specific relationship between FGF-2 and heparan sulfate of the MEC, a relationship which is not found with other GAGs.

On the structural level, investigations on this interaction have revealed that the minimum sequence on the heparan sulfate chain, required for binding FGF-2 is a pentasaccharide containing at least one $C_2$-sulfated iduronic acid residue and at least one N-sulfate group. Further, the presence on FGF-2 of a heparin sulfate binding site allows this interaction. This site is found at the level of two β sheets β10 and β11 sheets) containing several basic aminoacid residues. On FGF-2 a distinct site is also found for binding to their biological receptors: the FGFRs. Interaction of FGF with its signaling receptor involves dimerization of this receptor and the presence of heparin sulfate as co-receptor. The model of the response to FGF-2 sets forth the formation of binary complexes FGF-2/HSPG and then the instantaneous association of FGFR leading to the formation of a ternary complex which will undergo dimerization in order to provide in vivo biological activity via the protein kinase of the receptor (IBRAHIMI & coll., *Biochemistry*, 2004, 43, 4724-4730). This model was further supported by the discovery on FGFR of a heparin/heparin sulfate binding site.

Several heparan sulfate proteoglycans may bind FGF-2, these proteoglycans may either be attached to the surface of the cells, free in the MEC or on the basal membrane. Four of them have been listed in the literature. These are β-glycan, a membrane heparan sulfate proteoglycan which however has a stronger affinity for TGFβ; glypican, a heparan sulfate proteoglycan connected to the cell membrane through a glycosylphosphoinositol link; syndecan, a transmembrane heparan sulfate proteoglycan, having the most affinity for FGF-2; and perlecan, a heparan sulfate proteoglycan of the matrix.

Degradation of FGF-2 and Protection

FGF-2 is sensitive to proteolysis and may be degraded rapidly, even at a physiological temperature. The conditions for degradation of FGF-2 were investigated and described in the literature in the absence and in the presence of heparin (a natural highly sulfated GAG) which forms the standard control for its very strong affinity for FGF-2.

TARDIEU & coll., in 1992, (Tardieu and coll., *Journal of cellular Physiology*, 150:194-203; (1992)) investigated the behavior of (acid) FGF-1 and FGF-2 confronted with a change of pH. Three conditions were tested, with or without heparin beforehand: pH 2, pH 7 and pH 9. Degradation of FGF was investigated in a fibroblast proliferation model by radioactive element incorporation. The results show that FGF-2 is inactivated at acid pH and at basic pH but that with the presence of heparin it is possible to retain a similar (or even slightly weaker) activity of FGF-2 to that observed at neutral pH.

The authors have also investigated thermal degradation of FGF-1 and FGF-2 in this same model. FGF solutions, either in the presence of heparin or not, are incubated at 0° C., 20° C., 37° C., 60° C. and 90° C. for different times: 1 hr, 24 hrs, 7, 14, 30 and 60 days. The obtained results show that the activity of FGF-2 depends on temperature. Increasing the latter causes a reduction in the activity of FGF-2. Notably, at 60° C. and 90° C., no activity is detected, and this even in the presence of heparin. On the other hand, for the other investigated temperatures, heparin provides protection of the activity of FGF-2 over time.

Finally, enzymatic degradation of FGF-1 and FGF-2 was investigated confronted with trypsin and chymotripsin. After 3 hours of incubation at 37° C. of FGF solutions, either in the presence of heparin or not, an electrophoresis on 18% polyacrylamide gel was performed in order to view non-degraded FGF. The incubation time allows the totality of the FGF present in the samples to be degraded whether with trypsin or chymotripsin. On the other hand, with the presence of heparin it is possible to find the 18 kDa band relative to FGF-2, meaning total protection of FGF-2 by heparin.

In the same way, it was shown that GAGs stabilized the active conformation of FGF-2, protecting it from acid or even thermal denaturation and increasing the specific interaction with specific cell receptors. In the presence of heparin, the FGFs are more stable during storage and more resistant to denaturating and proteolytic conditions.

Taking into account the important role of FGF-2 in therapeutics, in healing, and tissue repair, and its sensitivity to different stresses, such as temperature and enzymatic proteolysis, teams have studied the effects of an additional supply of FGF-2 or even the protection of FGF-2 by natural or synthetic molecules.

Indeed, Yamanaka, in 2005 (Basic fibroblast growth factor treatment for skin ulcerations in scleroderma, cutis, 2005; 76:373-376), describes the topical use of recombinant FGF-2 for treating ulcers of the skin. FGF-2 stimulates the FGF receptors of the fibroblasts and induces activation of fibroblasts and vascular proliferation. During the repairing process, during the restructuring phase, FGF-2 would also act on the proliferation of keratinocytes.

Dextran derivatives were synthesized (Tardieu, 1992, cited earlier) for potentializing the activity of FGF-2 (mitogenic activity of fibroblasts), by protecting it against heat, denaturation with pH and enzymatic degradation (trypsin and chymotripsin). These derivatives show greater protection of FGF-2 than heparin, so that it is possible to have compounds which represent an alternative to the use of heparin which has a strong anticoagulant activity. They are stabilizers, potentializers, and protectors of the matrix for pharmaceutical formulations acting on the tissue repair. Further, Franck et al, in 2004 (*J. Biomater Sci. Polymer Edn.* Vol. 15. N°11, pp. 1463-1480(2004)), have shown that other derivatives of dextrans in a fibroblast culture may increase proliferation of the cells and promote the effect of the growth factor on cell growth.

Finally, Sylvia Colliec-Jouault et al., (*Exopolysaccharides produced by bacteria isolated from deep-sea hydrothermal vents: new agents with therapeutic potential, Pathologie Biologie*, 52, 127-130 (2004)), deal with the use of a particular exopolysaccharide neosynthesized by a bacteria which was used as an implant for bone filling in an experimental model in rats. After 15 days, the animals exhibited complete healing with no observed inflammatory reaction. This result would be explained by the interaction of the exopolysaccharide with soluble mediators including FGF-2; this would allow the proliferative activity of FGF-2 to be increased and thereby promote the healing phenomenon. This exopolysaccharide is used for dental healing.

The Skin: FGF-2, Proteoglycans and Aging

In the skin, FGF-2 is found at the epidermis, at the dermo-epidermal junction (JDE), at the dermis, the hypodermis and the capillaries; it has a wide activity spectrum. It ensures proliferation of the fibroblasts within the dermis so that they may thereby synthesize macromolecules of the matrix, essential to the integrity of the skin, but it also acts on other cells of the skin. Proliferation of melanocytes is actually controlled by this FGF-2 which also is a promoter for the formation of capillaries. At the fibroblasts, in addition to their proliferation, FGF-2 also increases the mRNA rate of the genes coding for hyaluronan synthase and thus increases production of hyaluronan, the main GAG of the dermis.

In injuries, FGF-2 is an important actor of the healing phenomenon. It acts at the fibroblast level, always by increasing their proliferation, but also on the keratinocytes in order to inhibit expression of collagenase-1 and thereby allow the skin to be reconstructed more rapidly. This action during healing does not occur with heparan sulfate as transporter/reservoir but with dermatan sulfate. Expression of FGF-2 is then mainly carried out by the keratinocytes, macrophages and fibroblasts. The half-life time of FGF-2 in vitro was assessed to be about 24 hours at 37° C. and at a neutral pH (SOMMER & RIFKIN, *Journal of cellular physiology* 138:215-220 (1989)). Thus, FGF-2 is an important cytokine of the skin because of the many functions which it fulfills.

The proteoglycans of the skin and their distribution were studied. The main GAGs revealed for their capability of interacting with FGF-2 are found in the skin. The quantitative and qualitative distribution of the GAGs was determined as follows: hyaluronic acid (31%), chondroitin sulfate (25%), keratan sulfate (24%), dermatan sulfate (20%) and finally heparan sulfate (18%). Heparan sulfate contained in the dermis allows the present FGF-2 to be stored.

During aging, the skin is subject to many physiological changes. In addition to wrinkles which form the most visible marks, there are deep structural changes which appear. The dermis notably atrophies, notably as a consequence of the reduction in the number of fibroblasts and in their synthesis potency, causing changes in the macromolecules of the extracellular matrix. A reduction in the synthesis of glycosaminoglycans is also reported involving reorganization of the present proteoglycans. In studies on fibroblast cultures, it was possible to show that the synthesis of hyaluronic acid strongly decreased during aging whereas that of keratan and chondroitin sulfates increased. As for dermatan and heparan sulfate, their synthesis would not stop decreasing. This decrease would no longer allow FGF-2 to be stored and therefore protect the endogenic potency of FGF-2.

OBJECT OF THE INVENTION

No document from the prior art has sought to protect a growth factor, notably FGF-2, from its degradation or denaturation notably taking place at the skin.

Thus, the object of the present invention is to solve the new technical problem consisting of completing the protective action of heparan sulfate proteoglycans by developing active ingredients which mimick the action of heparan sulfate, in order to protect endogenic supply of FGF-2, at the skin, and in particular at the dermis, and preferably capable of crossing the skin barrier to reach their target. Another object is to provide active ingredients which protect the endogenic amount of FGF-2, while making it available for renewing the extracellular matrix, and in particular the dermal matrix.

The object of the invention is notably to solve the technical problem consisting of providing active ingredients which protect FGF-2 from its degradation or denaturation, intervening in the various tissues and preferably at the skin, notably to provide cosmetic, dermo-cosmetic, or pharmaceutical compositions intended for restructuring the extracellular matrix by restructuration of the dermal matrix, for improving moisturization of the skin, promoting repair of the skin, maintaining the integrity of the dermis, improving the proliferation of melanocytes, reinforcing the epidermal differentiation, or reinforcing renewal of the epidermis, notably in humans.

The object of the present invention is to solve the new problem consisting of providing an active ingredient of plant origin, for solving the aforementioned problems. The active ingredients with which these technical problems may be solved, should not be toxic, or irritating towards the skin.

The object of the present invention is thus also to provide active ingredients solving the technical problems mentioned in the field of cosmetics, dermo-cosmetics, or pharmacy, in particular for a topical application in humans.

The object of the present invention is also to solve the new technical problem consisting of providing a method for screening active ingredients with which the aforementioned objects may be achieved. This screening method should preferably allow a large number of active ingredients to be screened together in a reproducible and reliable way.

SUMMARY OF THE INVENTION

In order to identify the active ingredients solving the aforementioned technical problems, the inventors developed an in vitro screening model with which FGF-2 protective activity may be demonstrated on a large number of substances to be screened, in particular faced with thermal degradation of FGF-2.

For protecting FGF-2, these active ingredients play a major role ensuring integrity of the extracellular matrix, and notably of the dermal matrix, by renewing the cell population of the fibroblasts. They are therefore first choice active ingredients for effectively controlling degradation of FGF-2, and for controlling, i.a., skin aging.

According to a first aspect, the present invention relates to the use of a substance which is neither a sulfated glycosaminoglycan (sulfated GAG) nor a structural analog of a sulfated GAG, protecting FGF-2 as an active ingredient in a cosmetic or dermo-cosmetic or pharmaceutical composition, in order to prevent or control at least one skin alteration related to degradation of FGF-2.

Preferably, the substance protecting FGF-2 is a plant extract and does not comprise any sulfated GAG or structural analogue to a sulfated GAG.

Advantageously, as said substance is selected from the group consisting of an extract of *Hibiscus Abelmoschus* or ambrette, an extract of rebokza, and extract of gougizi berries, an extract of banha, an extract of *lessonia*, an extract of mustard flour, an extract of wooyin, an extract of barley, an extract of sesame, or one of the combinations resulting from the association of at least two of the listed extracts.

Advantageously, FGF-2 is protected at the human skin and preferably at the JDE, and/or the dermis, and/or the hypodermis, and/or the epidermis, and/or the wall of skin blood vessels.

Advantageously, skin alterations related to degradation of FGF-2 occur at the human skin and preferably at the JDE, and/or the dermis, and/or the hypodermis, and/or the epidermis, and/or the wall of skin blood vessels.

Advantageously, said substance is an aqueous or hydroalcoolic extract in a solution obtained from 1 to 10% of a plant or a plant portion, in the dry condition, based on the weight of the total solution. Preferably, the aqueous extract is a hydroglycolic extract.

In particular, degradation of the growth factor results from at least one degradation, for example thermal degradation, which usually occurs at a physiological temperature or by exposure to heat, and/or an enzymatic degradation, notably by cathepsin G.

Advantageously, said substance or composition is used for stimulating proliferation of skin cells, in particular proliferation of fibroblasts and/or melanocytes, and/or for increasing the synthesis of at least one matrix component, in particular at least one type of collagen, and/or at least one specific protein of microfibrils, such as fibrillin 1 or 2 and/or fibulin 3 or 5 and/or at least one glycosaminoglycan (GAG), notably a sulfated GAG.

According to a particular embodiment, the substance or composition can be particularly useful for restructuring the extracellular matrix, particularly that of; the JDE, the wall of skin blood vessels, the hypodermis, the epidermis, and in particular of the dermis by restructuring the dermal matrix; for increasing moisturization of the skin, for promoting repair of the skin, for maintaining the integrity of the dermis, for improving epidermal differentiation and for reinforcing renewal of the epidermis, as well as any of the combination thereof.

These different uses described above are directed at preventing or controlling skin alterations related to degradation of FGF-2.

Advantageously, the concentration of said substance is a concentration effective for protecting FGF-2, especially when applied topically. Effective amounts of such substances when applied topically have been found to range between 0.01% and 10% by weight of the total composition.

The composition is useful as a cosmetic, dermo-cosmetic or pharmaceutical composition, notably for humans.

The substance according to the present invention is preferably a plant extract protecting FGF-2 from its degradation. Such plant extract may be an aqueous or hydroalcoholic, and preferably hydroglycolic extract.

In one preferred embodiment, the substance is an aqueous or hydroalcoholic extract of *Hibiscus Abelmoschus* obtained from the seed of *Hibiscus Abelmoschus*.

According to a second aspect, the present invention relates to the use of a substance for making a composition, notably a cosmetic, pharmaceutical or dermo-cosmetic composition, for protecting FGF-2 from its degradation, notably in the different uses listed above.

The present invention further relates to a method of cosmetic, pharmaceutical or dermo-cosmetic treatment using a composition defined above according to any of the embodiments, notably for achieving a treatment related to at least one of the different uses listed above.

DETAILED DESCRIPTION OF THE DRAWINGS

DETAILED DESCRIPTION OF THE PRESENT INVENTION

With the present invention, protection of FGF-2 by the proteoglycans of this same matrix may be obtained.

By "protection of FGF-2" is meant protection of FGF-2 against its degradation or denaturation. This degradation or denaturation generally occurs as a lysis due to environmental conditions, such as enzymatic or thermal lysis. This degradation or denaturation may occur because of the reduction of the protection provided by the proteoglycans.

The screening method according to the present invention allowed various active ingredients extracted from plants to be screened. No plant extract was described as protecting FGF-2 from its degradation at the skin, notably in humans, only substances with a structure close to heparan sulfate were used.

A particularly effective and unexpected active ingredient for protecting FGF-2 from thermal degradation was identified; this is an aqueous extract obtained from the seed of a plant belonging to the Malvaceae family, more particularly to the *Hibiscus* genus and even more particularly *Hibiscus Abelmoschus* or ambrette.

*Hibiscus abelmoschus* was notably known as an aqueous extract obtained from the whole plant, exclusively for its slimming properties in cosmetics, and more particularly for controlling cellulitis (see for example, U.S. Pat. No. 5,705,170).

Other extracts with the desired activity for the present invention were able to be selected. Their activity is particularly unexpected, notably as to the protection of FGF-2. The extracts are notably an aqueous extract of *Lycium chinense* or gougizi berries obtained from dehydrated entire berries, an aqueous extract of *Pinelliae ternata* or banha obtained from a tuber, an aqueous extract of *Raphanus sativus* or rebokza obtained from the seed, an extract of *Brassica juncea* or mustard obtained from the seed, an aqueous extract of *Coicis semen* or wooyin obtained from the seed, an extract of *Hordeum vulgare* or barley obtained from the seed, an extract of *Sesamum indicum* or golden sesame obtained from the seed, and an extract of an entire alga of *lessonia* sp. or *lessonia*.

These extracts are however not limited to the sole aqueous extracts. Thus, the present invention also covers any polar solvent with which the whole of the active compounds may be essentially obtained in an aqueous extract in order to provide the properties desired within the scope of the present invention. From tests made by the present inventors, the desired properties may be obtained with hydroglycolic extracts. An extraction solvent of the type water/glycol is preferred among the hydroglycolic extracts. A mixture water/butyleneglycol is particularly preferred.

The proportions of the water/alcohol mixture may vary as known to one skilled in the art. The water/alcohol proportions generally vary from 10/90 to 90/10, and for example from 50/50 to 85/15.

It is preferable to use in the present invention as an active ingredient, an extract in solution obtained from 1 to 10% of a plant or plant portion in the dry condition, based on the weight of the total solution.

The composition according to the present invention advantageously comprises from 0.001 to 20%, preferably from 0.01 to 10%, of active ingredient according to the present invention by weight of the total composition. The composition may be applied topically or administered orally.

The screening method of a potentially active substance for protecting FGF-2 as to its degradation in humans notably comprises:
a) placing a potentially active substance in contact with FGF-2 at a temperature of about 45° C. for a period of about 2 h,
b) selecting substances protecting FGF-2 from at least 50%, and preferably 65% of its degradation.

Advantageously, the screening method comprises an additional step for testing transcutaneous penetration in order to select an active substance crossing through the skin barrier.

Advantageously, the present invention relates to the method for preparing a composition, comprising the application of said screening method followed by a step for mixing the selected active substance with an excipient for preparing the composition.

Other objects, features and advantages of the invention will become clearly apparent to one skilled in the art upon reading the explanatory description which refers to examples which are only provided as an illustration and which may by no means limit the scope of the invention.

The examples are an integral part of the present invention and any feature appearing as novel relative to any prior state of the art, from the description taken as a whole, including the examples, is an integral part of the invention in its function and in its generality.

Thus, each example has a general scope.

In the examples, all the percentages are given by weight, unless stated otherwise, and temperature is expressed in degrees Celsius unless stated otherwise, and pressure is atmospheric pressure unless stated otherwise.

EXAMPLES

Example 1: Study of Thermal Degradation of FGF-2

Tardieu et al, in 1992 studied thermal degradation of FGF-2 in a fibroblast proliferation model by radioactive element incorporation. The present inventors have developed a method with which the stability of FGF-2 may be investigated: this quantification method which may be used on a large scale, allows achievement of screening of active ingredients, which would not have been possible with the method described by Tardieu.

A 5 ng/ml solution of FGF-2 in a 10 mM PBS buffer with 0.1% BSA and 0.1% of methylparaben is prepared.

This solution is placed at various temperatures: 4° C., 20° C., 37° C., 50° C., and 80° C. either in the presence of heparin or not at 500 µg/ml.

Dosages of FGF-2 with a commercial ELISA kit (R&D system, France) are performed at different times (T=0, 3 hrs, 24 hrs and 48 hrs) so as to establish degradation kinetics for each temperature of investigation.

The results are expressed as a percentage of FGF-2 relative to time T=0. The experiments are conducted in triplicates (n=3). The obtained results are illustrated in FIGS. 1 and 2.

FGF-2 is sensitive to the temperature conditions to which it is submitted.

Figure 1:
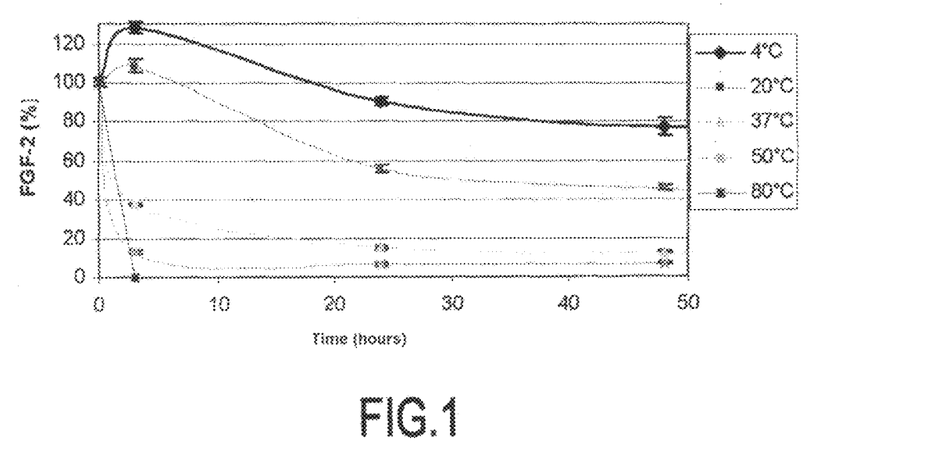
FIG. 1 is a graph of the time course of the stability of FGF-2 as a function of time at different temperatures.
Figure 2:
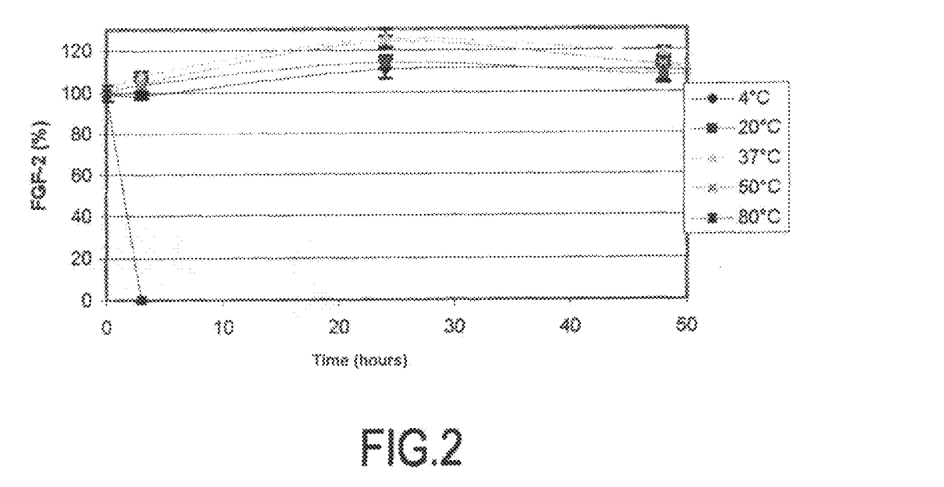
FIG. 2 is a graph of the stability of FGF-2 at various temperatures in the presence of heparin.

FIG. 1 shows the time course of the stability of FGF-2 as a function of time at different temperatures. FGF-2 stored at 4° C. is relatively stable over a period of 48 hrs since 20% of FGF-2 is degraded at that temperature. With increase in the temperature, the degradation percentages increase: after 3 hrs at 37° C., FGF-2 undergoes 65% degradation and 80% degradation at 50° C. Finally, after 3 hrs at 80° C., total degradation of FGF-2 is observed which is due to denaturation of the proteins at that temperature.

Finally, the longer the time and more the observed degradation is significant, after 24 hrs at 37° C., 80% of FGF-2 is degraded.

FIG. 2 illustrates the stability of FGF-2 at various temperatures in the presence of heparin. FIG. 2 shows that this degradation is stopped by the presence of 0.05% heparin which is the experimental positive control and which, by its strong affinity with FGF-2, stabilizes it. Heparin is a highly sulfated polysaccharide known for its very strong affinity with FGF-2.

This protection is not effective at 80° C. because heparin is also denaturated at that temperature.

Surprisingly, degradation of FGF-2 at about 50° C. occurs over a short time period. A temperature close to 45° C. is selected for practical purposes and is a selection parameter for achieving a stress model for screening active ingredients, the experimental positive control preferably consisting of heparin.

Example 2: In Vitro Model for Selecting an Active Protecting FGF-2 Against Thermal Degradation Degradation of FGF-2 observed at about 50° C. is particularly interesting, because a short period of time allows degradation of FGF-2 of about 80%, thereby allowing a large number of tests to be conducted. For this reason, it was decided to achieve screening with a stress of 2.15 hrs at 45° C. and to study the capacity of a large number of actives for protecting FGF-2 against this thermal degradation.

The applied screening model is the following:

180 µl of a 4.5 ng/ml FGF-2 solution prepared in 0.1% BSA/PBS buffer are distributed in a 96-well microplate. 20 µl of distilled water or 0.05% heparin or a solution containing various active ingredients extracted from different plants to be tested are added. The plate is stirred by means of a plate stirrer and then covered with adhesive tape and placed in an oven at 45° C. for 2.15 hrs. At the end of the incubation period, the plate is taken out and dosage of FGF-2 is then carried out by means of the ELISA kit.

A control plate only containing FGF-2 and distilled water, treated under the same conditions, is left at room temperature.

The results are expressed as a FGF-2 protection percentage relatively to the non-stressed or non-degraded FGF-2 control.

Example 3: Validation of the Model by GAGs and Proteoglycans of the Skin

Tests were carried out with commercially available GAGs and PGs in order to validate the model.

GAG solutions at different concentrations are made: heparan sulfate, dermatan sulfate, chondroitin sulfate, and hyaluronic acid are solubilized and tested at 0.1%, 0.01%, and 0.001%.

The heparin used as positive control is tested at 0.1%, 0.01%, 0.001%, 0.0001% and 0.00001%.

The tested proteoglycans are glypican-3 and decorin tested at 0.1%, 0.01%, and 0.001%.

The stress protocol described in Example 2 was applied, 20 µl of water being substituted with 20 µl of corresponding GAG or PG solution. The tested GAGs and PGs thereby undergo additional dilution to ¹⁄₁₀.

Figure 3:
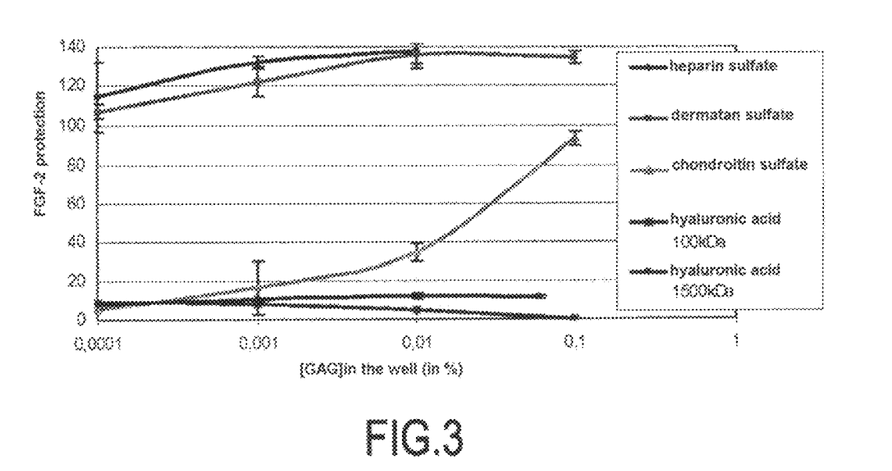
FIG. 3 is a graph showing FGF-2 protection by GAGs of the skin.

FIG. 3 illustrates the study of the FGF-2 protection by GAGs of the skin.

The results obtained in FIG. 3, confirm the data from the literature, i.e.:

Heparin sulfate protects FGF-2 as well as dermatan sulfate and this at each tested concentration. Indeed, it is dermatan sulfate which is the main promoter of FGF-2's activity during the healing process. Hyaluronan, regardless of its molecular weight, by no means allows FGF-2 to be protected. As for chondroitin sulfate, the protection which it provides depends on its dose but does not however reach 100%.

Figure 4:
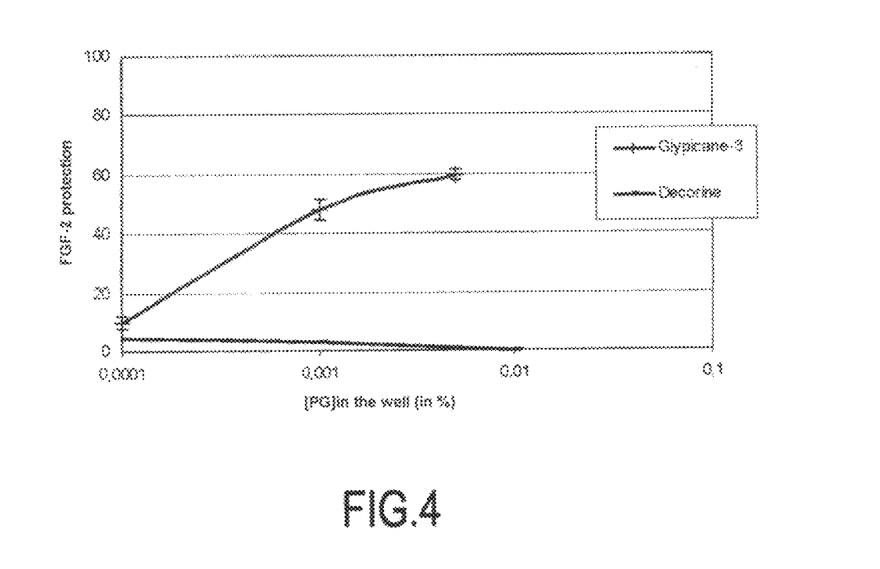
FIG. 4 is a graph showing the protection of FGF-2 by proteoglycans.

The test of 2 proteoglycans, in FIG. 4 (Study of the protection of FGF-2 by PGs), glypican-3 and decorin, confirmed the data from the literature. i.e. that glypican-3 which has heparan sulfate chains protects FGF-2 in a dose-dependent way, whereas decorin (consisting of chondroitin sulfate and dermatan sulfate chains) proves to be inefficient.

This study shows that protection of FGF-2 depends on the structure of the GAGs. Interaction of heparan sulfate to FGF-2 is validated properly. This interaction is confirmed when the PG bearing heparan sulfate chains is tested in the model.

This study enables our screening model to be validated by the confirmation of results from the literature.

Example 4: Screening of Active Ingredients

Screening was performed according to Example 2, from a library consisting of 2,000 plant extracts and featured molecules. These solubilized compounds, plant extracts, marine algae, or featured molecules, are tested pure, or at 10% or 1% in the reaction medium described in Example 2.

The results of the most efficient active ingredients are described in Table 1, below.

TABLE 1

Results obtained during screening

| Tested active ingredient Common name | Protection (%) Obtained for 10% active ingredient | Protection (%) Obtained for 1% active ingredient |
|---|---|---|
| Shallot extract | 95.07 | 1.2 |
| Soya flour extract | 86.85 | 67.66 |
| Urucum extract | 103.5 | 29.8 |
| White mustard extract | 110.5 | 17.39 |
| Plant lycopod extract | 71 | 11.27 |
| Lupin flour extract | 116.39 | 65.77 |
| Potato extract | 73 | 16.5 |
| Jioh extract | 70.9 | 23.18 |
| Garlic extract | 95.99 | 13.92 |
| Angelica extract, radicant variety | 72.5 | 7.31 |
| Mungo bean extract | 76.78 | 2.42 |
| *Ligusticum chuanxiong* extract | 70.53 | 38.15 |
| Carrot extract | 83.93 | 1.65 |
| *Hibiscus Abelmoschus* or ambrette extract | 135.1 | 87.53 |
| Parsnip extract | 92.89 | 23.15 |
| Pea extract | 74.33 | 0 |
| Potato extract | 88.96 | 3.61 |
| Orange extract | 70 | 2.83 |
| Sweet pepper extract | 87.35 | 28.44 |
| rebozka extract | 142.5 | 77.34 |
| Sea cucumber extract | 69.2 | |
| Gougizi beery extract | 154.4 | 68.59 |
| banha extract | 129.5 | 65.64 |
| lessonia extract | 53.3 | 61.79 |
| Mustard flour extract | 110.1 | 56.85 |
| wooyin extract | 106.1 | 56.18 |
| Barley extract | 79.7 | 53.81 |
| Sesame extract | 124.4 | 52.73 |
| Odorous Acore extract | 55.6 | 49.34 |
| Hongsan extract | 102.3 | 44.58 |

TABLE 1-continued

Results obtained during screening

| Tested active ingredient Common name | Protection (%) Obtained for 10% active ingredient | Protection (%) Obtained for 1% active ingredient |
|---|---|---|
| Odorous Acore extract | 77.7 | 43.24 |
| Luteolin extract | 67.7 | 43.17 |
| Bryone extract | 81 | 40.4 |
| Mounwhaja extract | 102 | 39.56 |
| Almond extract | 99.5 | 38.53 |
| *Ligusticum chuanxiong* extract | 70.5 | 38.15 |
| Chunnansung extract | 108.4 | 37.7 |
| Squash extract | 85.7 | 37.5 |
| Goborn extract | 71.1 | 37.8 |
| Bangpung extract | 117.9 | 36 |
| Ammonium acrylate extract | 54.9 | |
| Hesongja extract | 81.9 | 33.3 |
| Flax extract | 93.3 | 32.6 |
| Parsley extract | 97.4 | 30 |
| Poppy seed extract | 70.33 | 8.8 |
| Boksin extract | 75.69 | 27.56 |
| Sanyak extract | 63.05 | 16.78 |
| Yellow flax seed extract | 88.56 | 28.4 |
| *Porphyra Tenera* extract | 38.35 | 29.77 |
| *Lithotheminium* extract | 53.78 | 26.6 |

The above extracts are preferably obtained by maceration of a portion of the plant in a water/alcohol mixture, preferably water/glycol form 100/0 to 0/100 (v/v). Dilution is then carried out in this solvent or mixture of solvents.

Certain tested actives have a strong protective activity which further is dose-dependent.

Example 5: *Hibiscus Abelmoschus* (Ambrette) Extract

5a—a hydroalcoolic ambrette extract is made from 5% (w/w) milled seeds in refluxing ethanol. The extraction is carried out for 1 hr and then the solution is filtered, the ethanol is removed and the result is solubilized at 5% (w/w) in a water/glycol (75/25) mixture and then ultrafiltered on ceramic filters with different cut-off thresholds, and finally filtered at 0.45 µm.

5b—a hydroglycolic ambrette extract is made in a water (75%)/GG (25%) mixture, preferentially from 5% (w/w) milled seeds. Maceration is carried out for 1 night at 4° C. and then the solution is ultrafiltered on ceramic filters with different cut-off thresholds, and finally filtered at 0.45 µm. BG means butyleneglycol.

5c—an aqueous ambrette extract is made in water, preferably from 5% (w/w) milled seeds. Maceration is carried out for 1 night at 4° C. and then the solution is ultrafiltered on ceramic filters with different cut-off thresholds, and finally filtered at 0.45 µm Example 6: Gougizi Berry Extract A gougizi berry extract is preferably made in a water (75%)/BG (25%) mixture from 5% (w/w) dehydrated whole berries. Maceration is carried out for 1 night at 4° C. and then the solution is ultrafiltered on ceramic filters with different cut-off thresholds, and finally filtered at 0.45 µm.

Example 7: Banha Extract

A banha extract is preferably made in a water (75%)/BG (25%) mixture from 5% (w/w) tubers. Maceration is carried out for 1 night at 4° C. and then the solution is ultrafiltered on ceramic filters with different cut-off thresholds, and finally filtered at 0.45 µm.

Example 8: Rebokza Extract

A rebokza extract is preferably made in a water (75%)/BG (25%) mixture from 5% (w/w) seeds. Maceration is carried out for 1 night at 4° C. and then the solution is ultrafiltered on ceramic filters with different cut-off thresholds, and finally filtered at 0.45 µm.

Example 9: *Lessonia* Extract

A *lessonia* extract is preferably made in a water (75%)/BG (25%) mixture from 5% (w/w) whole algae. Maceration is carried out for 1 night at 4° C. and then the solution is ultrafiltered on ceramic filters with different cut-off thresholds, and finally filtered at 0.45 µm.

Example 10: Mustard Extract

A mustard extract is preferably made in a water (75%)/BG (25%) mixture from 5% (w/w) seed. Maceration is carried out for 1 night at 4° C. and then the solution is ultrafiltered on ceramic filters with different cut-off thresholds, and finally filtered at 0.45 µm.

Example 11: Woovin Extract

A wooyin extract is preferably made in a water (75%)/BG (25%) mixture from 5% (w/w) seed. Maceration is carried out for 1 night at 4° C. and then the solution is ultrafiltered on ceramic filters with different cut-off thresholds, and finally filtered at 0.45 µm.

Example 12: Barley Extract

A barley extract is preferably made in a water (75%)/BG (25%) mixture from 5% (w/w) seed. Maceration is carried out for 1 night at 4° C. and then the solution is ultrafiltered on ceramic filters with different cut-off thresholds, and finally filtered at 0.45 µm.

Example 13: Sesame Extract

A sesame extract is preferentially made in a water (75%)/BG (25%) mixture from 5% (w/w) seed. Maceration is carried out for 1 night at 4° C. and then the solution is ultrafiltered on ceramic filters with different cut-off thresholds, and finally filtered at 0.45 µm. Each extract (examples 5-13) was partly kept. The optional preservative, preferably consisting of a mixture of caprylyl glycol, phenoxyethanol, 1% hexylene glycol was finally added in either the presence of xanthan or not.

Example 14: Selection of the Active Ingredients or Plant Extracts

The most efficient extracts are selected and tested at different concentrations according to the screening of Example 2. The active ingredients used are the extracts from Examples 5-13, and are diluted by using a solvent (or a mixture of solvents) which have been used for extraction. A concentration range between 0.1% and 10% was tested in this solvent for studying the specificity of these active ingredients towards thermal degradation of FGF-2. The dosages are carried out in triplicates. The obtained results are listed in Table 2, below:

TABLE 2

Effect vs. Doses obtained on ingredients or actives selected during screening

| | Protection of FGF-2 (in %) as a function of active ingredient concentration | | | | | |
|---|---|---|---|---|---|---|
| Active ingredient | 0.1% | 1% | 2% | 3% | 5% | 10% |
| *Hibiscus Abelmoschus* (ambrette) extract | 84.7 ± 6.03 | 87.5 ± 4.16 | 99.6 ± 3.17 | 110.9 ± 4.9 | 123.6 ± 1.48 | 130.8 ± 2.49 |
| Rebokza extract | 8.5 ± 1.6 | 72.3 ± 5.64 | 99.9 ± 5.47 | 106.6 ± 3.21 | 123.8 ± 1.43 | 129.4 ± 0.89 |
| Gougizi berry extract | 7.7 ± 0.5 | 29.5 ± 3.47 | 38 ± 4.14 | 52 ± 2.17 | 75 ± 3.05 | 109.4 ± 6.34 |
| Banha extract | 8 ± 1.46 | 52.5 ± 4.1 | 76.6 ± 2.57 | 85.5 ± 2.45 | 91 ± 2.82 | 98.9 ± 0.75 |
| *Lessonia* sp. extract | 13.2 ± 1.63 | 36 ± 5.49 | 50.8 ± 3.16 | 53.27 ± 3.04 | 53.67 ± 4.49 | 52.15 ± 0.84 |
| Codex flour mustard extract | 14.7 ± 2.86 | 88.7 ± 8.06 | 104.9 ± 5.01 | 111.3 ± 2.93 | 119 ± 1.2 | 118 ± 2.8 |
| Wooyin extract | 9.4 ± 0.95 | 56.4 ± 2.97 | 69.2 ± 0.88 | 80.6 ± 2.43 | 92.9 ± 4.39 | 102.4 ± 1.85 |
| Barley extract | 10.7 ± 0.95 | 47.4 ± 1.86 | 60.8 ± 2.31 | 70.2 ± 0.59 | 82.5 ± 0.4 | 97.8 ± 1.09 |
| *Sesame* extract | 2.3 ± 1.06 | 21.5 ± 0.43 | 48.4 ± 1.71 | 55.7 ± 19.44 | 74.8 ± 0.54 | 94.8 ± 1.7 |

The extracts are very effective and all have a dose-dependent activity therefore expressing an activity specificity of each active on the given target.

The *Hibiscus Abelmoschus* (ambrette) extract has the strongest activity and is therefore a select active ingredient in the protection of the growth factor FGF-2.

In Examples 15-21, the Active Ingredient Concentration (Extract 5c) is in Volume (v/v) Percent in Water Example 15: Study of the Protection of FGF-2 by the Aqueous Extract of *Hibiscus Abelmoschus* (Ambrette) Prepared According to Example 5c (Extract 5c)

An investigation on the protection of FGF-2 by the extract 5c was conducted on 2 industrial batches. The protection was investigated, confronted with a stress according to the conditions of Example 2.

The positive control consisting of tested 0.01% heparin in the final reaction medium after prior dilution in water protects by 105.52%±3.04.

The obtained results are listed in the Table 3, below:

TABLE 3

Protection of FGF-2 at 45° C. by 2 industrial batches of extract 5c

Protection of FGF-2 (in %) as a function of active ingredient concentration

| Extract 5c | 0.1% | 0.5% | 1% | 2% | 3% |
|---|---|---|---|---|---|
| Batch 1 | 4.78 ± 3.89 | 46.47 ± 1.85 | 81.01 ± 4.53 | 107.83 ± 2.53 | 120.76 ± 2.61 |
| Batch 2 | 4.38 ± 2.3 | 42.04 ± 2.76 | 69.6 ± 3.56 | 101.81 ± 4.02 | 118.67 ± 4.12 |

Extract 5c protects FGF-2 in a dose-dependent way with strong activity for 1% active ingredient concentration in water. The results obtained on 2 industrial batches are substantially identical.

It was absolutely necessary to check whether the extract 5c was able to protect FGF-2 at a physiological temperature, i.e., 37° C. This is why an investigation consisted of dosing FGF-2 after 24 hrs at 37° C. in the absence or in the presence of increasing concentrations of extract 5c.

A positive control formed by 0.01% heparin protects by 110.53%±3.20.

The obtained results are listed in Table 4, below:

TABLE 4

Protection of FGF-2 at 37° C. by 2 industrial batches of extract 5c

Protection of FGF-2 (in %) as a function of active ingredient concentration

| Extract 5c | 0.01% | 0.1% | 0.25% | 0.5% | 0.75% | 1% |
|---|---|---|---|---|---|---|
| Batch 1 | 8.37 ± 4.2 | 17.81 ± 3.04 | 51.02 ± 4.75 | 82.62 ± 1.98 | 108.39 ± 4.18 | 110.69 ± 13.28 |
| Batch 2 | 2.12 ± 1.17 | 20.56 ± 2.29 | 55.49 ± 2.61 | 91.06 ± 0.87 | 110.64 ± 2.45 | 122.87 ± 5.75 |

The obtained results show that the extract 5c protects FGF-2 at a physiological temperature and in a dose-dependent way. The extract 5c at this temperature further protects FGF-2 which is less degraded than at 45° C.

Example 16: Relates to the Study of Cytotoxicity of Extract 5c on Monolayer Fibroblasts Via a PNPP Dosage The object was to investigate cytotoxicity of extract 5c on normal human fibroblasts.

This dosage is based on the transformation of p-nitrophenyl phosphate (PNPP) into p-nitrophenol by intracellular acid phosphatases of viable cells. Absorbance of p-nitrophenol at 405 nm is directly proportional to the number of viable cells contained in the culture wells.

Once the confluence of the normal human fibroblasts is reached, the culture media were replaced with 200 μl/well of supplemented medium or not (control) of the extract 5c with increasing concentrations: 0.1; 0.5; 1; 2; 3 and 5%.

The cells were incubated for 48 hrs in an oven at 37° C.

After incubation and removal of the culture media, the cells were rinsed twice with PBS (phosphate buffered solution) and then put into the presence of 200 μl of a buffer containing 0.1 M sodium acetate (pH 8), 0.1% Triton X-100 and 5 mM p-nitrophenyl phosphate (Sigma, France). After two hours of incubation at 37° C. in an atmosphere containing 5% $CO_2$, the reaction was stopped by adding 20 μl of 1N NaOH. The absorbance of the reaction media at 405 nm was then determined by means of a plate-reader (Victor[2] V, Perkin Elmer, Finland).

Non-enzymatic hydrolysis of p-nitrophenyl phosphate was determined during each experiment on wells which did not contain any cells ("blank"). All the measurements were made in sextuplicates (n=6).

The obtained results are listed in Table 5, below:

TABLE 5

Study of cytotoxicity of normal human fibroblasts

| Extract 5c concentration (%) | Percentage of viable cells as compared with the negative control |
|---|---|
| 0.1 | 85.9 |
| 0.5 | 88.7 |
| 1 | 88.8 |
| 2 | 87.5 |
| 3 | 89.8 |
| 5 | 85.5 |

Extract 5c is not cytotoxic in all the tested range of concentrations.

Example 17: Study of Fibroblast Proliferation by FGF-2 Protected by the Extract 5c The purpose of this study was to check that FGF-2 protected by the extract 5c stimulates proliferation of normal human fibroblasts.

A solution of FGF-2 is prepared extemporaneously (=non-degraded FGF-2); a solution of FGF-2 is placed for 24 hrse at 37° C. in the absence (=degraded FGF-2) and in the presence of heparin (=FGF-2+heparin at 37° C.) at 0.01%.

Each FGF-2 solution is diluted so as to be applied on the cells, the final FGF-2 concentrations being the following: 0.1, 0.25, 0.5, 0.75 and 1 ng/ml.

Normal human dermal fibroblasts were sown at low density in 6-well plates. They were then grown in a medium in the absence (control) or in the presence of FGF-2 at various concentrations.

After 48 hrs, the activity of intracellular acid phosphatases (PNPP) is dosed, so as to be able to evaluate the effect of FGF-2 solutions, either treated or not, on cell proliferation.

The results are expressed as a proliferation percentage relative to the control well i.e. to the non-treated well.

The obtained results are illustrated in Table 6 below and in FIG. 5:

TABLE 6

Study of proliferation (expressed as percent relative to the non-treated well) obtained after treatment with various non-degraded FGF-2 concentrations, different degraded FGF-2 concentrations and different FGF-2 concentrations + heparin at 37° C.

| FGF-2 concentration (ng/ml) | Non-degraded FGF-2 | Degraded FGF-2 | FGF-2 + heparin at 37° C. |
|---|---|---|---|
| 0.1 | 116.7 ± 0.012 | 96.2 ± 0.014 P = 0.006** | 129.3 ± 0.009 |
| 0.25 | 138.7 ± 0.005 | 111 ± 0.006 P < 0.001*** | 154.8 ± 0.01 |
| 0.5 | 148.5 ± 0.007 | 123.7 ± 0.005 P < 0.001*** | 146.8 ± 0.007 |
| 0.75 | 163.2 ± 0.005 | 132.5 ± 0.004 P < 0.001*** | 149.8 ± 0.016 |
| 1 | 160 ± 0.003 | 146.4 ± 0.01 P = 0.003** | 148.1 ± 0.006 |

Figure 5:
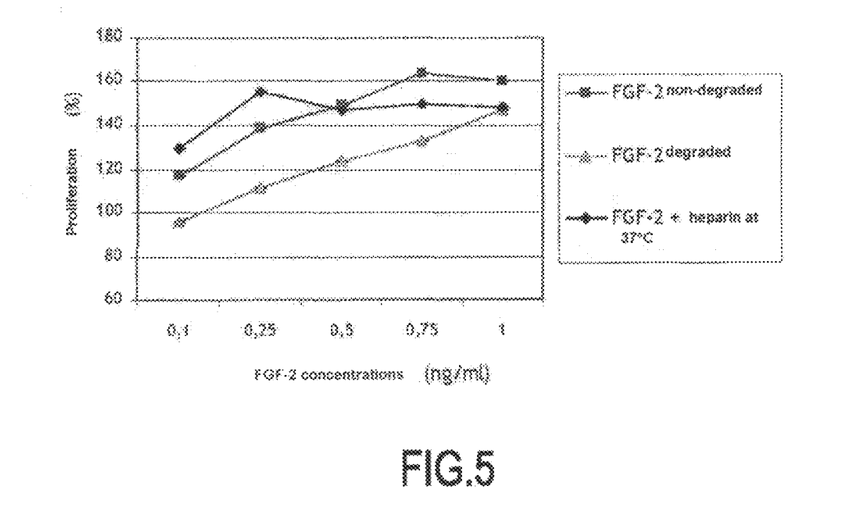
FIG. 5 illustrates a study of the proliferation of fibroblasts in the presence of non-degraded FGF-2, degraded FGF-2 and FGF-2 + heparin at 37° C.

FIG. 5 illustrates a study of the proliferation of fibroblasts in the presence of of non-degraded FGF-2, degraded FGF-2 and FGF-2+heparin at 37° C.

The results obtained show that FGF-2 (non-degraded) stimulate proliferation of normal human fibroblasts in a culture and this in a dose-dependent way.

FGF-2 degraded at 37° C. stimulates proliferation but in a much weaker way than FGF-2 non-degraded at 37° C. Indeed, for each tested concentration, proliferation and presence of degraded FGF-2 is statistically lower than that obtained with non-degraded FGF-2.

This example shows the relevance of developing an active capable of protecting the FGF-2 of the matrix which is degraded at a physiological temperature which may no longer assume its role of renewing dermal cells.

By protecting FGF-2 from thermal degradation, heparin used at 0.01% allows the FGF-2 to retain its biological properties since proliferation is maintained, or is even larger than that obtained with the FGF-2 solution prepared extemporaneously; up to the concentration of 0.5 ng/ml.

The very significant stimulation and the presence of heparin observed with small amounts of FGF-2 are not observed with more significant amounts of FGF-2.

The same experiment was conducted by replacing heparin with extract 5c. The FGF-2 solution put into the presence of 0.5% of extract 5c is placed for 24 hrs at 37° C. The solution is then diluted so as to apply 0.5 ng/ml of FGF-2 in the wells containing the fibroblasts.

The 5c extract concentration finally applied on the cells is 0.0025%. It was checked beforehand that this 5c extract concentration was not capable of inducing stimulation of the proliferation of fibroblasts. This means that the observed stimulation of proliferation is actually due to the protection of FGF-2 by extract 5c (see Table 8).

The obtained results expressed as a percentage of proliferation relative to the non-treated control, are shown in Table 7, below:

TABLE 7

Study of the proliferation (as a percentage) of fibroblasts obtained in the presence of non-degraded FGF-2 at 0.5 ng/ml, degraded FGF-2 at 0.5 ng/ml and FGF-2 + 0.5% 5c extract at 37° C.

| FGF-2 concentration | Non-degraded FGF-2 | Degraded FGF-2 | FGF-2 + 5c extract at 37° C. |
|---|---|---|---|
| 0.5 ng/ml | 148.5% ± 0.007 | 123.7% ± 0.005 P < 0.001*** | 143.8% ± 0.007 ns relative to non-stressed FGF-2 |

Figure 6:
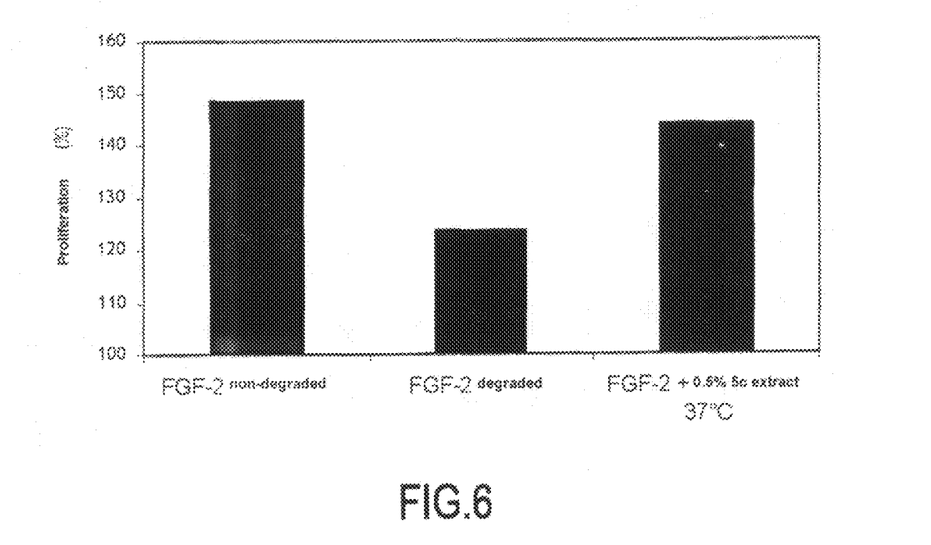
FIG. 6 illustrates the study of proliferation of fibroblasts in the presence of non-degraded FGF-2 at 0.5 ng/ml, degraded FGF-2 at 0.5 ng/ml and FGF-2 in the presence of the 5c extract at 0.5% at 37° C.

FIG. 6 illustrates the study of proliferation of fibroblasts in the presence of non-degraded FGF-2 at 0.5 ng/ml, degraded FGF-2 at 0.5 ng/ml and FGF-2 in the presence of the 5c extract at 0.5% at 37° C.

Co-incubation of FGF-2 and of the extract 5c at 37° C. provides protection of FGF-2 which retains its capabilities of stimulating proliferation of cultivated normal human fibroblasts. With the obtained results, it is possible to obtain fibroblast proliferation which is not statistically different from that obtained in the presence of FGF-2 prepared extemporaneously.

The benefit of an active with which FGF-2 may be protected, seems to be of major interest for cell renewal of fibroblasts.

A study of the proliferation of normal human fibroblasts in the presence of increasing concentrations of extract 5c was conducted for 48 hrs at 37° C.

The fibroblasts are sown in the presence of the 5c extract at various concentrations 0.0025%, 0.01%, 0.25%, 0.5%, 1% and 2%. After 48 hrs, dosage of acid phosphatases is carried out (PNPP dosage) at 405 nm and then proliferation is calculated (as a %) relative to the negative control (=non-treated cells). Each condition is tested in sextuplicates (n=6).

The obtained results are listed in Table 8, below:

TABLE 8

Study of fibroblast proliferation in the presence of the 5c extract

| 5c extract concentration (%) | Proliferation (in %) vs. negative control |
|---|---|
| 0.0025 | 100 |
| 0.01 | 99 |
| 0.25 | 107 |
| 0.5 | 114 |
| 1 | 111 |
| 2 | 122* |

*Significative One Way Analysis of Variance/Dunnett

The positive control consisting of 10% serum provides stimulation of proliferation significatively which validates the experiment (T+=+126%* of proliferation).

The obtained results show that the 5c extract does not stimulate proliferation of normal human fibroblasts in a culture.

Example 18: Impact of the Protection of Growth Factors on the Synthesis of Collagen Normal human fibroblasts stemming from a 52 year old donor, were cultivated in 96-well plates with a medium (consisting of DMEM, glutamine 2 mM, penicillin 50 IU/ml-streptomycin 50 µg/ml, 10% of fetal calf serum) for 24 hrs. After incubation, the cells were treated with the products consisting of vitamin C at 20 µg/ml (positive control) and the 5c extract at 2% and 1%, for 48 hrs. A control was made in parallel with medium only.

After 24 hrs of contact, radioactive proline (3H-proline) is added to the medium.

At the end of the experiment, the supernatants are collected for dosing the incorporation of radioactive praline into the intracellular proteins.

The obtained results are shown in Table 9, below:

TABLE 9

Study of the stimulation of collagen synthesis by the 5c extract

| Products | cpm | sd | n | % control | p |
|---|---|---|---|---|---|
| Control | 5981 | 829 | 6 | 100 | — |
| Vitamin C-20 µg/ml | 10185 | 287 | 3 | 170 | p < 0.01 |
| 5c extract 2% | 7342 | 273 | 3 | 123 | p < 0.01 |
| 5c extract 1% | 7056 | 783 | 3 | 118 | p < 0.01 |

Cpm: counts per minutes
Sd: standard deviation
n: test number
p: significance threshold The 5c extract tested at 2% and 1% was capable of stimulating synthesis of collagen in normal human fibroblasts and this significantly.

The obtained results show that the protection of the growth factors of the medium and of those synthesized by the fibroblasts, enables the synthesis of collagen to be stimulated in vitro.

Example 19: Impact of the Protection of Growth Factors on the Synthesis of Total GAGs and Sulfated GAGs The purpose of this study was to determine whether by protecting the growth factors with the 5c extract on monolayer fibroblast cultures, it was possible to stimulate synthesis of total GAGs by a radioactive method.

Normal human fibroblasts stemming from a 52 year old donor, were grown in 96-well plates with medium (consisting of DMEM, glutamine 2 mM, penicillin 50 IU/ml-streptomycin 50 µg/ml, 10% fetal calf serum) for 24 hrs. After incubation, the cells were treated with products consisting of vitamin C at 20 µg/ml (positive control) and the 5c extract at 2% and 1%, for 72 hrs. A control was made in parallel with the medium only.

After 48 hrs of contact, radioactive glucosamine (D-(6-$^3$H)-glucosamine) is added to the medium.

At the end of the experiment, the supernatants are collected for dosing the incorporation of radioactive glucosamine into the intracellular proteins. Dosage of the proteins is performed with a commercial kit (BioRad 500-0116).

The results are listed in the following Table 10:

TABLE 10

Study of the stimulation of synthesis of total GAGs by the 5c extract

| Products | Activity (cpm) | Proteins (mg/ml) | Ratio (act./Prot.) | % control | p |
|---|---|---|---|---|---|
| Control | 1059 | 3.579 | 296 | 100 | — |
| TGF-β 10 ng/ml | 2590 | 3.650 | 709 | 240 | P < 0.01 |
| 5c extract 2% | 4173 | 3.058 | 1365 | 461 | P < 0.01 |
| 5c extract 5c 1% | 1787 | 3.396 | 526 | 178 | P < 0.01 |

The obtained results show that the 5c extract applied at 2% and 1% on normal human fibroblasts was capable of stimulating synthesis of total GAGs with a dose effect and this more significantly than the positive control (TGF-β applied at 10 ng/ml).

The obtained results show that the protection of the growth factors of the medium and of those synthesized by fibroblasts enable the synthesis of total GAGs to be stimulated in in vitro In the same way, a study of the incorporation of $^{35}$S-sulfate is conducted for quantifying the sulfated GAGs. The applied procedure is the same as that for the total GAGs, except for the nature of the radioactive precursor. The results are listed in the Table 11, below:

TABLE 11

Study of the stimulation of the synthesis of sulfated GAGs by the 5c extract

| Products | Activity (cpm) | Proteins (mg/ml) | Ratio (act./Prot.) | % control | p |
|---|---|---|---|---|---|
| control | 3028 | 3.579 | 846 | 100 | — |
| TGF-β 10 ng/ml | 5442 | 3.650 | 1491 | 176 | P < 0.01 |
| 5c extract 2% | 5586 | 3.058 | 1827 | 216 | P < 0.01 |
| 5c extract 5c 1% | 4300 | 3.396 | 1266 | 150 | P < 0.01 |

The obtained results show that the extract 5c enables the synthesis of sulfated GAGs to be stimulated very significantly and in a dose-dependent way.

This means that in addition to the mimicking role plaid by the extract 5c towards FGF-2, the extract 5c is capable by protecting the growth factor of stimulating the synthesis of sulfated GAGs and the protection of FGF-2 may therefore be reinforced since these are the same heparan sulfated GAGs which protect FGF-2.

Example 20: Study of the Protective Activity of FGF-2 by the 5c Extract after Transcutaneous Permeation The purpose was to ensure that the 5c extract retained its properties of protecting the growth factor after having penetrated the skin.

A pure solution of the 5c extract was deposited on the surface of skin explants, mounted as Franz cells.

Figure 7:
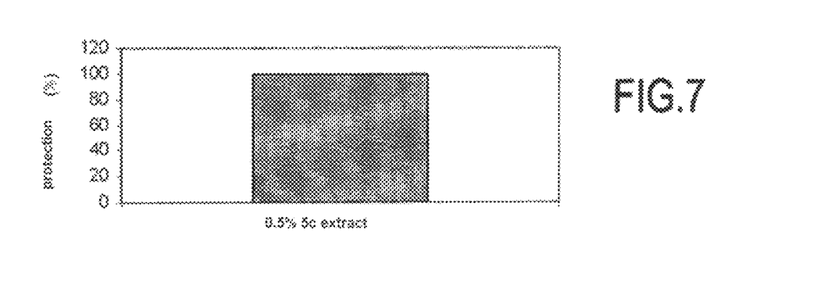
FIG. 7 illustrates the study of the FGF-2 protection by the 5c extract after passing through the skin.

After 24 hrs of incubation, the media contained in the receiving compartments of the cells were recovered and lyophilized. The lyophilisates were then dissolved in distilled waters so as to be finally tested in the model described in Example 15 with a thermal stress at 37° C. for 24 hrs.

FIG. 7 illustrates the study of the FGF-2 protection by the 5c extract after passing through the skin.

The obtained results (99.96% protection) show that the extract 5c integrally retained its protection properties since the obtained result is identical with that obtained in Table 4 of Example 15.

The results show after having penetrated the skin tissues, the extract 5c is capable of protecting the growth factors and therefore remains integer for reaching its target.

Example 21: Study of the Protection of FGF-2 Against Enzymatic Degradation

The purpose of this study is to quantify the degradation of FGF-2 by proteinases present at the dermis of human skin. These enzymes play an important role in the degradation of the extracellular matrix.

Notably, cathepsin G which intervenes during inflammation and is secreted in the extracellular environment. It strongly adheres to the cell surfaces of the matrix because of the basicity. Cathepsine G is also active against collagen but also to the core protein of proteoglycans and glycoproteins of the matrix.

For this reason, a study of the degradation of FGF-2 by cathepsin G was conducted. Degradation kinetics was carried out in a 100 mM Hepes buffer, pH7 containing 0.1% BSA. Cathepsin G was added into the wells of the plate at a concentration of 0.02 U per well to a 2 ng/well FGF-2 solution. The plate was incubated at 37° C. and sampling was performed at 15, 30, 60, 90 and 120 minutes in order to dose the remaining FGF-2.

The control (100%) is made by extemporaneous dosage of FGF-2. At the same time, an enzyme-free control solution is placed at 37° C. in order to study thermal degradation at the different times, so as to get rid of this degradation due to temperature and to quantify the portion only due to enzymatic degradation.

The amounts of FGF-2 (pg/ml) obtained are described in Table 12, below:

TABLE 12

Study of the degradation of FGF-by cathepsin G.

| Time (minutes) | FGF-2 concentration Temperature control | FGF-2 concentration in the presence of cathepsin G (Degradation %) |
| --- | --- | --- |
| 0 | 391.8 ± 3.64 | 339.05 ± 7.43 (13.29%) |
| 15 | 324.99 ± 1.7 | 295.61 ± 8.49 (8.95%) |
| 30 | 291.83 ± 2.4 | 248.04 ± 1.97 (14.77%) |
| 60 | 280.64 ± 3.23 | 203.67 ± 1.13 (27.5%) |
| 90 | 259.81 ± 4.9 | 141.94 ± 5.14 (45.55%) |
| 120 | 241.67 ± 1.97 | 131.36 ± 2.49 (45.6%) |

With the obtained results, it is possible to show that degradation of FGF-2 is increased with time. The enzyme enables the FGF-2 to be degraded very significantly at 90 minutes This is why this time will be selected for studying FGF-2 protection in the presence of cathepsin G by the 5c extract.

Various concentrations of extract 5c, i.e.: 0.01%, 0.05%, 0.1%, 0.5% and 1% are added to the reaction medium as described earlier (Example 21).

After 90 minutes at 37° C., the FGF-2 concentrations are assessed and the percentages of remaining FGF-2 as well as the protection percentages of FGF-2 are calculated. For each tested concentration, the dosage is performed with n=9. The results are described in Table 13, below:

TABLE 13

Study of the protection by the extract 5c of FGF-2 degraded by cathepsin G.

| Tests | FGF-2 concentration (pg/ml) | Remaining FGF-2 (%) | FGF-2 protection (%) |
| --- | --- | --- | --- |
| Control (100%) | 455.23 | 100 | — |
| Degraded control (enzyme) | 288.11 | 63.29 | 0 |
| 5c extract 0.01% | 336.93 | 74.01 | 29.21 |
| 5c extract 0.05% | 344.65 | 75.71 | 33.83 |
| 5c extract 0.1% | 409.08 | 89.86 | 72.38 |
| 5c extract 0.5% | 414.02 | 90.95 | 75.33 |
| 5c extract 1% | 406.58 | 89.31 | 70.89 |

The 5c extract is capable of protecting FGF-2 against enzymatic degradation in a dose-dependent way.

By this in vitro study it is possible to demonstrate that application of the 5c extract may protect growth factors from the proteolytic degradation exerted by the enzymes of the extracellular matrix. This only reinforces the benefit of the use of extract 5c in cosmetics.

Example 22: Detection of the FGF-2 Rate with Age

The purpose of this study was to study the FGF-2 concentration of so-called "young" and so-called "old" skins in order to establish a relationship between age and the loss of FGF-2 content mainly due to the change in skin GAG content.

Skin biopsies stemming from so-called young donors (21, 30, 31 and 38 years of age) and stemming from so-called old (50, 55, 57 and 58 years of age) were sampled and extracted after milling in a PBS buffer, pH 7, containing 0.1% Triton X100, in order to perform dosage of FGF-2 with a commercial ELISA kit (R&D System, DFB50). The FGF-2 concentration is related to the DNA rate measured by a commercial kit Picogreen.

Figure 8:
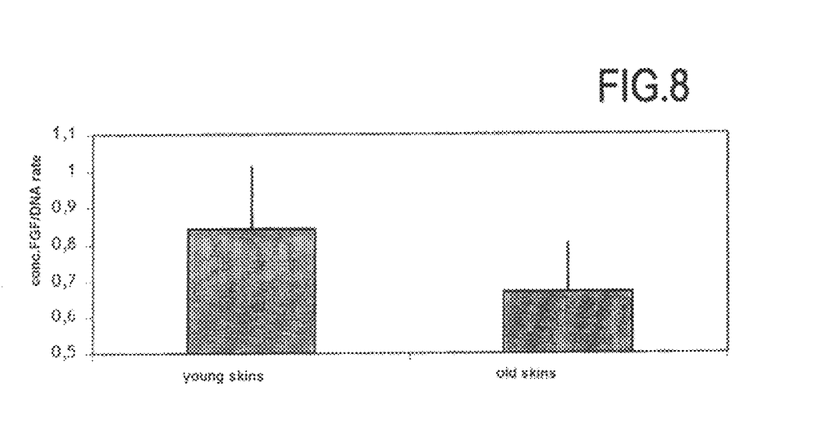
FIG. 8 illustrates a study of the FGF-2 concentration in so-called "young" and "old" skin hydrolysates.

The results obtained are illustrated in FIG. 8:

FIG. 8 illustrates a study of the FGF-2 concentration in so-called "young" and "old" skin hydrolysates.

The results show a difference in the FGF-2 content between young skins and old skins. Further, this difference is statistically significant (p=0.046).

With this example, it is possible to show that by using an active as a protective agent of growth factors and more particularly of FGF-2, it is possible to control effects related to skin aging.

Example 23: Formulation of the Inventive Products

One proceeds according to methods known to one skilled in the art, with mixing together different portions A, B, C, D, E, or F for preparing a composition according to the present invention. The <<inventive products>> represent the active ingredients mentioned in the present invention.

Use of inventive products in cosmetic or pharmaceutical formulations of the oil-in-water emulsion type.

Formulation 23a:

| | | |
|---|---|---|
| A | Water | qsp 100 |
| | Butylene glycol | 2 |
| | Glycerin | 3 |
| | Sodium Dihydroxycetyl Phosphate, Isopropyl Hydroxycetyl Ether | 2 |
| B | glycol Stearate SE | 14 |
| | Triisononaoin | 5 |
| | Octyl Cocoate | 6 |
| C | Butylene glycol, Methylparaben, Ethylparaben, Propylparaben, pH adjusted to 5.5 | 2 |
| D | Inventive products | 0.01-10% |

Formulation 23b:

| | | |
|---|---|---|
| A | Water | qsp 100 |
| | Butylene glycol | 2 |
| | Glycerin | 3 |
| | Polyacrylamide, isoparaffin, Laureth-7 | 2.8 |
| B | Butylene glycol, methylparaben, ethylparaben, propylparaben; | 2 |
| | Phenoxyethanol, methylparaben, propylparaben, butylparaben, ethylparaben | 2 |
| | Butylene glycol | 0.5 |
| D | Inventive products | 0.01-10% |

Formulation 23c:

| | | |
|---|---|---|
| A | Carbomer | 0.50 |
| | Propylene glycol | 3 |
| | Glycerol | 5 |
| | Water | qsp 100 |
| B | Octyl cocoate | 5 |
| | Bisabolol | 0.30 |
| | Dimethicone | 0.30 |
| C | Sodium hydroxide | 1.60 |
| D | Phenoxyethanol, methylparaben, propylparaben, butylparaben, ethylparaben | 0.50 |
| E | Perfume | 0.30 |
| F | Inventive products | 0.01-10% |

Example 24 of the Invention

Use of Inventive Products in a Formulation of the Water-in-Oil Type

| | | |
|---|---|---|
| A | PEG 30 - dipolyhydroxystearate | 3 |
| | Capric triglycerides | 3 |
| | Cetearyl octanoate | 4 |
| | Dibutyl adipate | 3 |
| | Grape seed oil | 1.5 |
| | Jojoba oil | 1.5 |
| | Phenoxyethanol, methylparaben, propylparaben, butylparaben, ethylparaben | 0.5 |
| B | Glycerin | 3 |
| | Butylene glycol | 3 |
| | Magnesium sulfate | 0.5 |
| | EDTA | 0.05 |
| | Water | qsp 100 |

| | | |
|---|---|---|
| C | Cyclomethicone | 1 |
| | Dimethicone | 1 |
| D | Perfume | 0.3 |
| E | Inventive products | 0.01-10% |

Example 25 of the Invention

Use of the Inventive Products in a Formulation of the Shampoo or Shower Gel Type

| | | |
|---|---|---|
| A | Xantham gum | 0.8 |
| | Water | qsp 100 |
| B | Butylene glycol, methylparaben, ethylparaben, propylparaben | 0.5 |
| | Phenoxyethanol, methylparaben, propylparaben, butylparaben, ethylparaben | 0.5 |
| C | Citric acid | 0.8 |
| D | Sodium laureth sulfate | 40.0 |
| E | Inventive products | 0.01-10% |

Example 26 of the Invention

Use of the inventive products in a formulation of the lipstick type and other anhydrides products

| | | |
|---|---|---|
| A | Mineral wax | 17.0 |
| | Isostearyl isostearate | 31.5 |
| | Propylene glycol dipelargonate | 2.6 |
| | Propylene glycol isostearate | 1.7 |
| | PEG 8 beewax | 3.0 |
| | Hydrogenated palm kernel oil glycerides, Hydrogenated palm glycerides | 3.4 |
| | Lanoline oil | 3.4 |
| | Sesame oil | 1.7 |
| | Cetyl lactate | 1.7 |
| | Mineral oil, lanolin alcohol | 3.0 |
| B | Castor oil | qsp 100 |
| | Titanium dioxide | 3.9 |
| | CI 15850:1 | 0.616 |
| | CI 45410:1 | 0.256 |
| | CI 19140:1 | 0.048 |
| | CI 77491 | 2.048 |
| C | Inventive products | 0.01-5% |

Example 27 of the Invention

Use of the inventive products in a formulation of aqueous gels (eye contours, slimming agents, etc.)

| | | |
|---|---|---|
| A | Water | qsp 100 |
| | Carbomer | 0.5 |
| | Butylene glycol | 15 |
| | Phenoxyethanol, methylparaben, propylparaben, butylparaben, ethylparaben | 0.5 |
| B | Inventive products | 0.01-10% |

Example 28 of the Invention

Use of the Inventive Products in a Formulation of the Triple Emulsion Type

| | Primary emulsion W1/O | |
|---|---|---|
| A | PEG 30 - dipolyhydroxystearate | 4 |
| | Capric triglycerides | 7.5 |
| | Isohexadecane | 15 |
| | PPG-15 stearyl ether | 7.5 |
| B | Water | 65.3 |
| C | Phenoxyethanol, methylparaben, propylparaben, butylparaben, ethylparaben | 0.7 |
| | Secondary emulsion W1/O/W2 | |
| A | Primary emulsion | 60 |
| B | Poloxamer 407 | 2 |
| | Phenoxyethanol, methylparaben, propylparaben, 2-bromo-2-nitropropane-1,3-diol | 0.3 |
| | Water | qsp 100 |
| C | Carbomer | 15 |
| D | Triethanolamine | PH 6.0-6.5 |

Example 29 of the Invention

Preparation of Pharmaceutical Formulations Containing the Inventive Product

Formulation 29a: Preparation of Tablets

| A | Excipients | In g per tablet |
|---|---|---|
| | Lactose | 0.359 |
| | Saccharose | 0.240 |
| B | Inventive products* | 0.001-0.1 |

*The inventive product is obtained for example according to the extraction procedure described in Example 5c followed by a drying step.

Formulation 29b: Preparation of an Ointment

| A | Excipients | |
|---|---|---|
| | Low density polyethylene | 5.5 |
| | Liquid paraffin | qsp 100 |
| B | Inventive products* | 0.001-0.1 |

*The inventive product is obtained for example according to the extraction procedure described in Example 5c followed by a drying step.

Formulation 29c: Preparation of an Injectable Formulation

| A | Excipient | |
|---|---|---|
| | Salted isotonic solution | 5 ml |
| B | Inventive products* | 0.001-0.1 g |

*The inventive product is obtained for example according to the extraction procedure described in Example 5c followed by a drying step.

Example 30: Assessment of the Cosmetic Acceptance of a Preparation Containing the Inventive Product Toxicological tests were carried out on the compound obtained according to Example 5c, by skin an eye assessment in rabbits, by studying the absence of abnormal toxicity by single oral administration in rats and by studying the sensitizing potency on guinea-pigs.

Assessment of Primary Skin Irritation in Rabbits:

The preparations described in Example 5c, are applied without dilution at a dosage of 0.5 ml on the skin of 3 rabbits according to the method recommended by the OECD directive relating to the study of "acute irritating/corrosive effect on the skin".

The products are classified according to the criteria defined by the order as of 1.2.1982 published in the JORF (French Official Journal) of 21.02.82.

The results of these tests provide the conclusion that the products of the invention were classified as non-irritating for the skin.

Assessment of Eye Irritation in Rabbits:

The preparations described above were instilled pure one at a time, in an amount of 0.1 ml, in the eye of 3 rabbits according to the method recommended by the OECD directive NO. 405 of Feb. 24, 1987 relating to the study of <<acute irritating/corrosive effect on eyes>>.

The results of these tests provide the conclusion that the preparations may be considered as non-irritating for the eyes, in the sense of the 91/326 EEC directive either used pure or without being diluted.

Test on the Absence of Abnormal Toxicity by Single Oral Administration in Rats:

The described preparations were administered once orally at the dosage of 5 g/Kg of body weight, to 5 male rats and 5 female rats according to a procedure inspired by the OECD directive No. 401 as of Feb. 24, 1987 and adapted to cosmetic products.

DL0 and DL50 were found to be larger than 5,000 mg/Kg. The tested preparations are therefore not classified among preparations dangerous by ingestion.

Assessment of the Skin Sensitization Potency in Guinea-Pigs

The described preparations were subject to the maximization test described by Magnusson and Kligmann, a protocol in accordance with guide-line No. 406 of the OECD.

The preparations are classified as non-sensitizing by contact with the skin.

The invention claimed is:

1. A method for protecting FGF-2 in aging human skin, the method comprising applying to the skin a cosmetic composition comprising an effective amount of an extract of seeds of *Hibiscus abelmoschus* obtained by using a solvent consisting essentially of water or a water/alcohol mixture, wherein said solvent has a ratio of water to alcohol from 85/15 to 100/0, and a cosmetically acceptable excipient.

2. The method of claim 1, wherein the effective amount is between 0.001% and 20% by weight based on the total weight of the cosmetic composition.

3. The method of claim 2, wherein the effective amount is between 0.01% and 10% by weight of the total cosmetic composition.

4. The method of claim 1, wherein the alcohol is ethanol.

5. The method of claim 1, wherein the solvent has a ratio of water to alcohol from 85/15 to 90/10.

6. A method for protecting FGF-2 in aging human skin, the method comprising applying to the skin a cosmetic composition comprising an effective amount of an extract of seeds of *Hibiscus abelmoschus* obtained by using a solvent consisting essentially of water or a water/alcohol mixture, wherein said solvent has a ratio of water to alcohol from 85/15 to 100/0, and a cosmetically acceptable excipient, wherein said effective amount is an amount sufficient to protect FGF-2 against thermal degradation.

7. The method of claim 6, wherein said extract is an aqueous extract of *Hibiscus abelmoschus* obtained by macerating the seeds of *Hibiscus abelmoschus* in water.

8. The method of claim 7, wherein the water used for macerating the seeds of *Hibiscus abelmoschus* is at a low temperature.

9. The method of claim 8, wherein the low temperature is 4° C.

10. The method of claim 6, wherein the solvent has a ratio of water to alcohol from 85/15 to 90/10.

11. The method of claim 6, wherein the effective amount is between 0.001% and 20% by weight based on the total weight of the cosmetic composition.

12. The method of claim 6, wherein the effective amount is between 0.01% and 10% by weight of the total cosmetic composition.

13. The method of claim 6, wherein the alcohol is ethanol.

14. A method for protecting FGF-2 in aging human skin, the method comprising applying to the skin a cosmetic composition comprising an effective amount of an extract of the seeds of *Hibiscus abelmoschus* obtained by using water as solvent and a cosmetically acceptable excipient.

15. The method of claim 14, wherein the extract of the seeds of *Hibiscus abelmoschus* is obtained by using water at a low temperature as solvent.

16. The method of claim 15, wherein the low temperature is 4° C.

* * * * *